(12) United States Patent
Yamaguchi

(10) Patent No.: US 10,249,480 B2
(45) Date of Patent: Apr. 2, 2019

(54) TANDEM MASS SPECTROMETRY DATA PROCESSING SYSTEM

(71) Applicant: SHIMADZU CORPORATION, Kyoto-shi, Kyoto (JP)

(72) Inventor: Shinichi Yamaguchi, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 52 days.

(21) Appl. No.: 15/112,453

(22) PCT Filed: Jan. 20, 2014

(86) PCT No.: PCT/JP2014/050947
§ 371 (c)(1),
(2) Date: Jul. 19, 2016

(87) PCT Pub. No.: WO2015/107690
PCT Pub. Date: Jul. 23, 2015

(65) Prior Publication Data
US 2016/0343557 A1  Nov. 24, 2016

(51) Int. Cl.
*H01J 49/00* (2006.01)
*H01J 49/40* (2006.01)
*H01J 49/42* (2006.01)
*G06F 19/00* (2018.01)

(52) U.S. Cl.
CPC ........ *H01J 49/0036* (2013.01); *G06F 19/703* (2013.01); *H01J 49/0045* (2013.01);
(Continued)

(58) Field of Classification Search
USPC .......................... 250/282; 702/23; 422/68.1
See application file for complete search history.

(56) References Cited

U.S. PATENT DOCUMENTS

| 8,481,924 B2 | 7/2013 | Savitski et al. |
| 2005/0063864 A1 | 3/2005 | Sano et al. |

(Continued)

FOREIGN PATENT DOCUMENTS

| JP | 61-20856 A | 1/1986 |
| JP | 2011-520129 A | 7/2011 |

(Continued)

OTHER PUBLICATIONS

International Search Report of PCT/JP2014/050947 dated Apr. 22, 2014.
(Continued)

*Primary Examiner* — Lam S Nguyen
(74) *Attorney, Agent, or Firm* — Sughrue Mion, PLLC

(57) ABSTRACT

Peak information is collected from an MS/MS spectrum in which the product ions generated from ions originating from a plurality of compounds are mixed. Using one of the m/z values of a plurality of ion species as precursor-ion information and the peak information of the MS/MS spectrum as product-ion information, a database search is performed to find candidate compounds for each compound, and a standard MS/MS spectrum of each candidate compound is obtained. For each combination of the candidate compounds, a virtual MS/MS spectrum is created by integrating the standard MS/MS spectra of those candidate compounds, and the degree of similarity between the virtual MS/MS spectrum and the measured MS/MS spectrum is calculated. If the candidate compounds are correct compounds, the degree of similarity will be high. Accordingly, the compound names and other results are visually presented to users in descending order of the degree of similarity.

2 Claims, 9 Drawing Sheets

(52) U.S. Cl.
CPC .......... *H01J 49/40* (2013.01); *H01J 49/4225* (2013.01); *G06F 19/705* (2013.01)

(56) References Cited

U.S. PATENT DOCUMENTS

2013/0304394 A1    11/2013   Yamaguchi
2013/0306857 A1*   11/2013   Yamaguchi ........... H01J 49/004
                                                       250/282

FOREIGN PATENT DOCUMENTS

| JP | 2012-122871 A | 6/2012 |
| WO | 2006/049064 A1 | 5/2006 |
| WO | 2009/138179 A2 | 11/2009 |

OTHER PUBLICATIONS

A. R. Ledvina et al., "Increased Throughout of Proteomics Analysis by Multiplexing High-Resolution Tandem Mass Spectra", Analytical Chemistry, 2011, vol. 83, pp. 7651-7656, XP055213064.

Communication dated Jan. 2, 2017, issued by the European Patent Office in corresponding European Application No. 16185384.1.

Haiying Zhang et al., "Mass defect filter technique and its applications to drug metabolite identification by high-resolution mass spectrometry", J. Mass. Spectrom., 2009, vol. 44, pp. 999-1016, XP055330389.

Christophe Masselon et al., "Accurate Mass Multiplexed Tandem Mass Spectrometry for High-Throughput Polypeptide Identification from Mixtures", Analytical Chemistry, Apr. 15, 2000, vol. 72, No. 8, pp. 1918-1924, XP002908490.

Communication dated Jan. 2, 2017, issued by the European Patent Office in corresponding European Application No. 14879070.2.

Written Opinion for PCT/JP2014/050947 dated Apr. 22, 2014. [PCT/ISA/237].

Communication dated Feb. 7, 2017 from the Japanese Patent Office in counterpart Application No. 2016-104352.

Communication dated Sep. 27, 2018, issued by the European Patent Office in corresponding European Application No. 14879070.2.

* cited by examiner

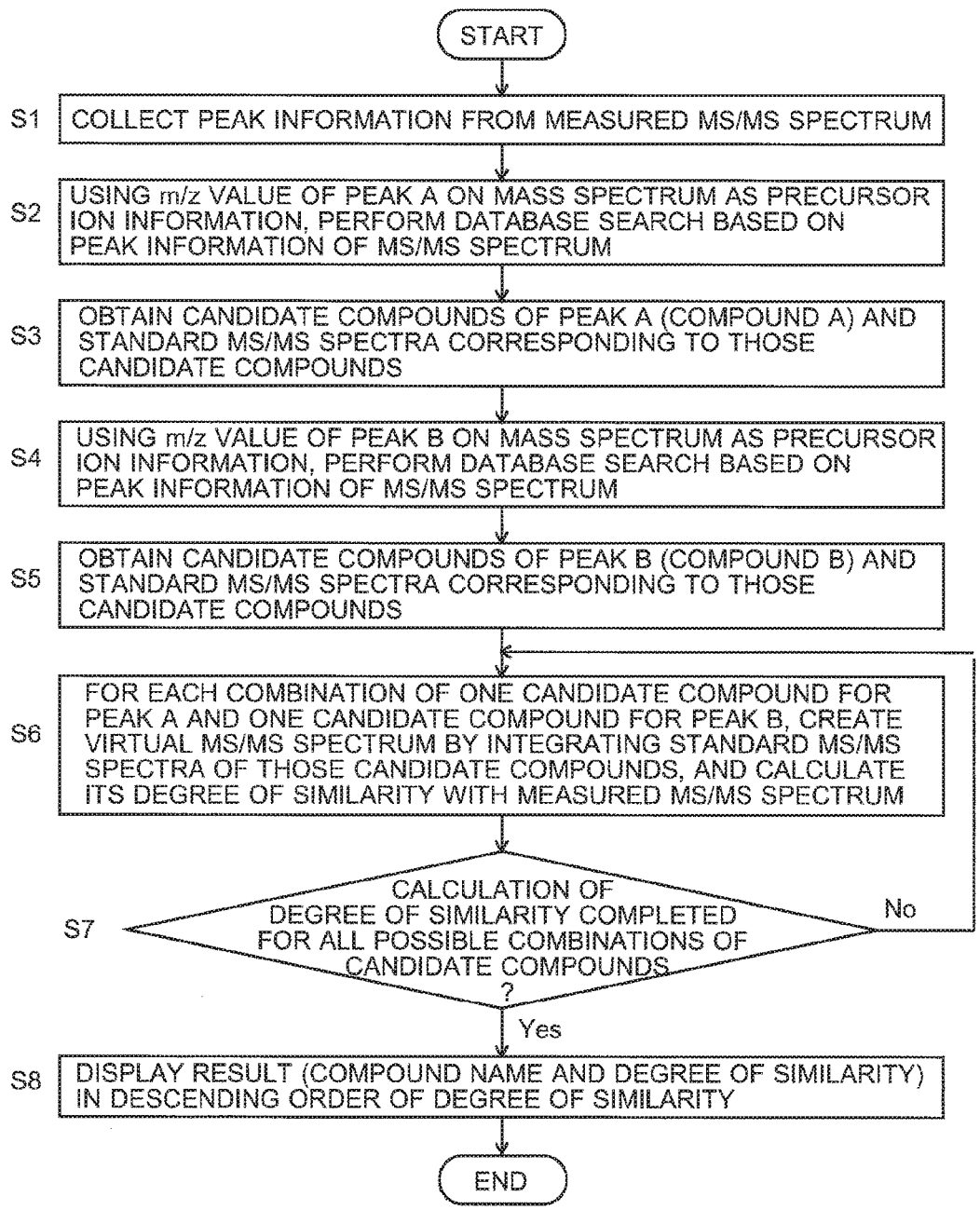

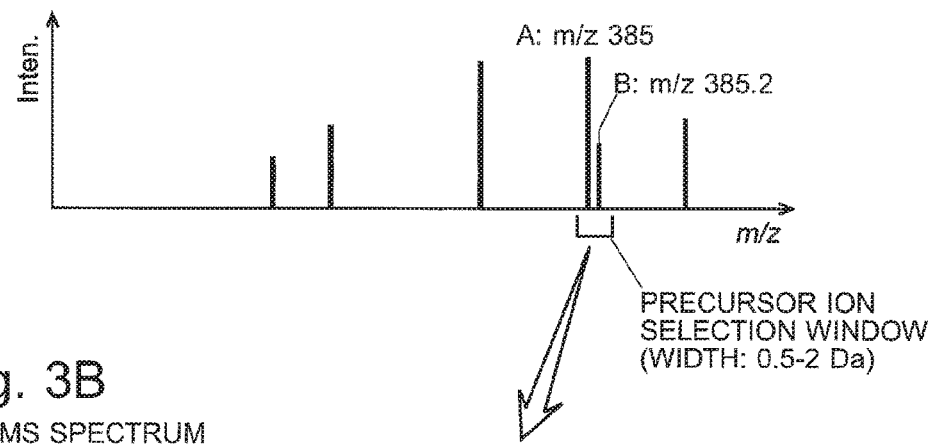
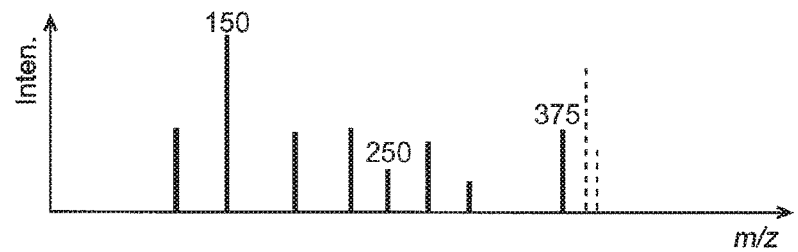

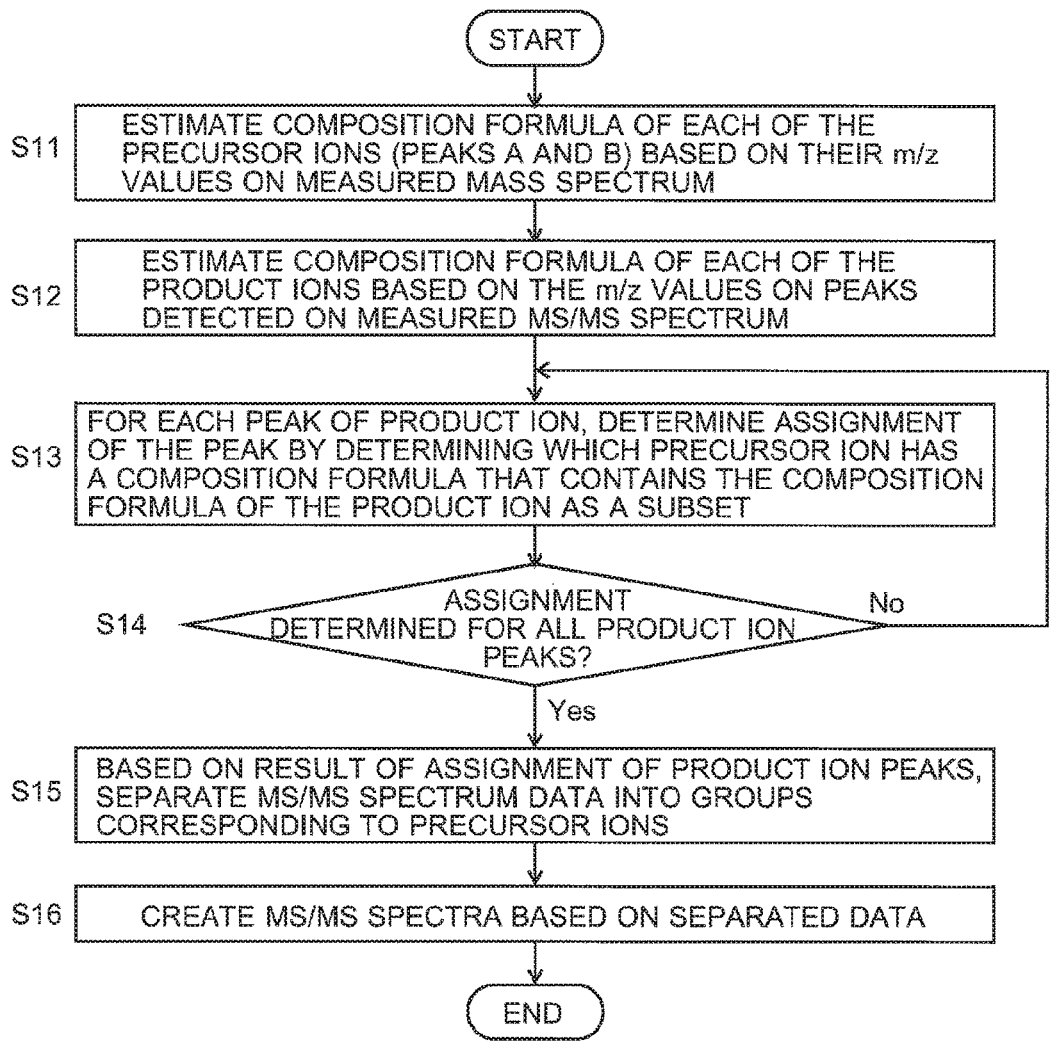

Fig. 7A
MS/MS SPECTRUM
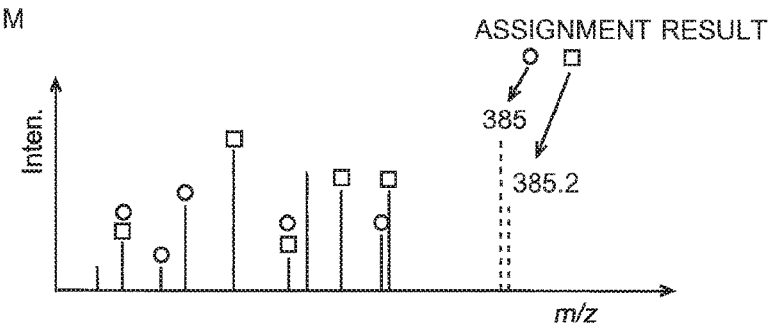
Fig. 7B
RECONSTRUCTED MS/MS SPECTRA
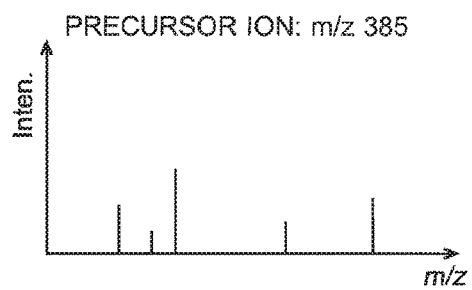
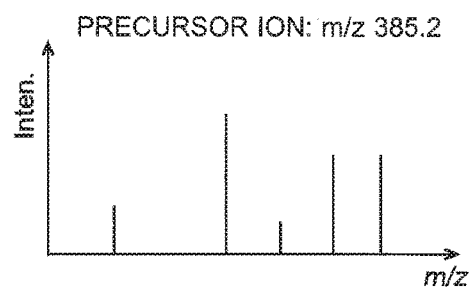

Fig. 9A
COMPOUNDS
Triallate : C₁₀H₁₆Cl₃NOS   304.0091  → mass defect 0.0091
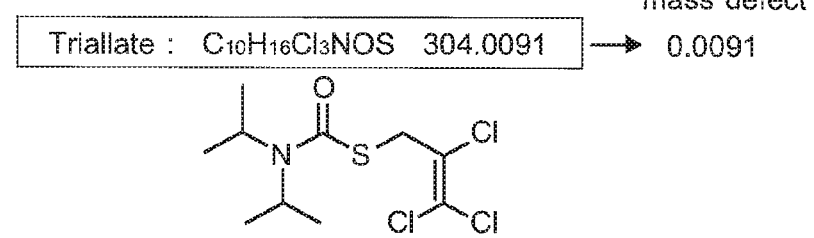
Fenpropimorph : C₂₀H₃₃NO   304.2635  → 0.2635
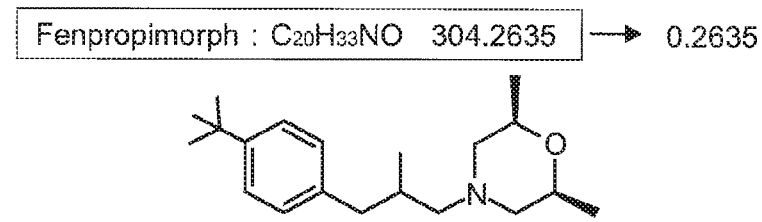
Fig. 9B
PRODUCT ION a
C₄H₉NOS   119.0405  → mass defect 0.0405
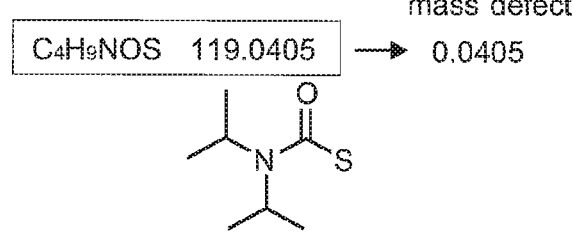
Fig. 9C
PRODUCT ION b
C₁₄H₂₂   190.3245  → 0.3245
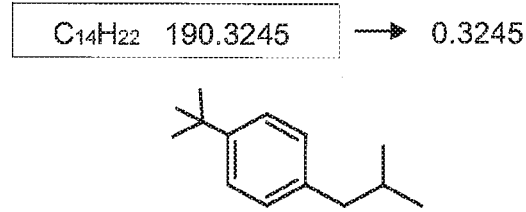

TANDEM MASS SPECTROMETRY DATA PROCESSING SYSTEM

CROSS REFERENCE TO RELATED APPLICATIONS

This application is a National Stage of International Application No. PCT/JP2014/050947 filed Jan. 20, 2014, the contents of which are incorporated herein by reference in its entirety.

TECHNICAL FIELD

The present invention relates to a data processing system for processing data collected with a tandem mass spectrometer capable of fragmenting an ion and performing a mass spectrometry of the ions generated by the fragmentation.

BACKGROUND ART

As one technique of the mass spectrometry, a technique called the "tandem analysis" or "$MS^n$ analysis" is commonly known. The tandem analysis is an analytical technique including the following steps: an ion having a specific mass-to-charge ratio as the target is initially selected from various ions generated from the compounds in a sample; the selected ion (which is normally called the "precursor ion") is fragmented by a collision-induced dissociation (CID) or similar dissociating operation; and a mass spectrometry for the ions generated by the fragmentation (which are normally called the "product ions") is performed. In recent years, this technique has been widely used, mainly for the identification and structural analysis of substances having high molecular weights. For some compounds that cannot be broken into sufficiently small fragments by a single dissociating operation, the selection of the precursor ion and the dissociating operation for that precursor ion may be repeated a plurality of times (i.e. an $MS^n$ analysis with n being equal to or greater than three may be performed).

Examples of the commonly known mass spectrometers for tandem analysis include a triple quadrupole mass spectrometer having two quadrupole mass filters placed on the front and rear sides of a collision cell (which is also called the "tandem quadrupole mass spectrometer") as well as a Q-TOF mass spectrometer using a time-of-flight mass analyzer in place of the rear quadrupole mass filter in the triple quadrupole mass spectrometer. These types of mass spectrometers can perform the selection and dissociation of the precursor ion only one time, and therefore, only a tandem analysis of up to $MS^2$ (=MS/MS) analysis can be performed. By comparison, in the case of an ion trap mass spectrometer using an ion trap which is capable of repeatedly performing the selection and dissociation of the precursor ion a plurality of times, or an ion-trap time-of-flight mass spectrometer including an ion trap combined with a time-of-flight mass spectrometer, it is in principle possible to perform an $MS^n$ analysis with no limitation of the value of n (although n is practically limited to five or so for the sake of sensitivity).

The process of identifying a compound in a sample using such a tandem analysis is normally performed as follows: An ion having a specific mass-to-charge ratio originating from the compound is fragmented, and a mass spectrometry for the product ions generated by the fragmentation is performed to obtain an $MS^2$ spectrum. The peak pattern of this measured $MS^2$ spectrum is compared with those of the $MS^2$ spectra of known compounds stored in a compound database, and the degree of similarity of the pattern is calculated. With reference to this degree of similarity, the kind of compound is determined. Therefore, for an exact identification of the compound, it is essential that the peak information observed in the mass spectrum (primarily, the mass-to-charge-ratio values) be highly accurate. In recent years, the performance of mass spectrometers has noticeably improved, and a peak which is merely observed as a single peak on a mass spectrum obtained with a conventional device can often be resolved into a plurality of peaks with a device having a high mass-resolving power. With such an improvement in the mass-resolving power and mass accuracy, the reliability of the compound identification by the previously described database search has also dramatically improved.

While the mass-resolving power of the device has improved in the previously described manner, it is difficult to extremely decrease the mass-to-charge-ratio width which is set for selecting the precursor ion. The reason for this is because the selection characteristics of the window for extracting an ion having a specific mass-to-Charge ratio ("mass window") show a comparatively gradual change (i.e. the transmittance gradually decreases) at both end portions of the window, which means that narrowing the mass-to-charge-ratio selection width of the window decreases the amount of product ions to be subjected to the dissociating operation, making it difficult to detect the product ions with a sufficiently high level of sensitivity (for example, see Patent Literature 1). For such reasons, in commonly used mass spectrometers, the mass-to-charge-ratio selection width for the precursor ion is set at approximately 0.5-2 Da, Therefore, if there are a plurality of kinds of ions with a small difference in mass-to-charge ratio (e.g. 0.5 Da or smaller), a plurality of peaks of the product ions created by the dissociation of a plurality of different ion species will be mixed on the eventually obtained $MS^2$ spectrum. If the peak information derived from such an $MS^2$ spectrum is simply used in the database search, it will be difficult to identify the compound with a sufficiently high level of accuracy.

CITATION LIST

Patent Literature

Patent Literature 1: JP 2012-122871 A

SUMMARY OF INVENTION

Technical Problem

As just described, conventionally, even when it is previously known that there are a plurality of peaks originating from different kinds of ion species within a narrow mass-to-charge-ratio range on a mass spectrum ($MS^1$ spectrum), it is often inevitable to perform the dissociating operation for the entire group of the peaks, so that only an $MS^2$ spectrum in which the product ions generated from the different ion species are mixed can be obtained. On such an $MS^2$ spectrum, it is difficult to discriminate between the product-ion peaks originating from the different ion species. Therefore, it has been difficult to improve the accuracy of the identification of the compound by database search.

Such a problem typically occurs in $MS^2$ spectra, although a similar situation can occur with any $MS^n$ spectra with n being equal to or greater than three.

The present invention has been developed to solve such a problem. Its first objective is to provide a tandem mass spectrometry data processing system capable of identifying a plurality of compounds using an MS$^n$ spectrum (with n being equal to or greater than two) in which the peaks of the product ions obtained by dissociating ions originating from a plurality of different compounds are mixed.

Solution to Problem

The first mode of the tandem mass spectrometry data processing system according to the present invention developed for achieving the aforementioned objective is a tandem mass spectrometry data processing system for processing MS$^n$ spectrum data obtained by performing a mass spectrometry for product ions obtained by dissociating ions collectively selected as precursor ions, the precursor ions originating from a plurality of different compounds and having mass-to-charge ratios within a predetermined mass-to-charge-ratio width, the system including:

a) a compound database in which at least information on standard MS$^n$ spectra related to known compounds is stored;

b) a peak information collector for collecting peak information from an MS$^n$ spectrum created based on the MS$^n$ spectrum data obtained by an actual measurement;

c) a database searcher for finding a candidate compound for each of the ions of the plurality of compounds selected as the precursor ions, by performing a database search over the compound database based on the mass-to-charge-ratio value of the ion concerned and the peak information collected from an MS$^n$ spectrum by the peak information collector; and d) a similarity calculator for retrieving, from the compound database, the standard MS$^n$ spectra for the candidate compounds selected for each of the ions of the plurality of compounds, for assuming a combination of the candidate compounds for the plurality of compounds, for creating a virtual MS$^n$ spectrum in which the standard MS$^n$ spectra corresponding to the candidate compounds included in the assumed combination are integrated with each other, and for calculating the degree of similarity between the virtual MS$^n$ spectrum and the measured MS$^n$ spectrum for each combination of the candidate compounds, wherein the plurality of compounds is identifiable using the degree of similarity obtained by the similarity calculator.

The second mode of the tandem mass spectrometry data processing system according to the present invention which has also been developed for achieving the aforementioned objective is a tandem mass spectrometry data processing system for processing MS$^n$ spectrum data obtained by performing a mass spectrometry for product ions obtained by dissociating ions collectively selected as precursor ions, the precursor ions originating from a plurality of different compounds and having mass-to-charge ratios within a predetermined mass-to-charge-ratio width, the system including:

a) a compound database in which at least information on standard MS$^n$ spectra related to known compounds is stored;

b) a peak information collector for collecting peak information from an MS$^n$ spectrum created based on the MS$^n$ spectrum data obtained by an actual measurement;

c) a database searcher for finding a candidate compound for each of the ions of the plurality of compounds selected as the precursor ions, by calculating the mass of a neutral loss which is the difference between the mass-to-charge-ratio value of the ion concerned and a mass-to-charge ratio known from the peak information collected by the peak information collector, and performing a database search over the compound database based on the mass-to-charge ratio of the precursor ion concerned and the mass of the neutral loss; and d) a similarity calculator for retrieving, from the compound database, the standard MS$^n$ spectra for the candidate compounds selected for each of the ions of the plurality of compounds, for assuming a combination of the candidate compounds for the plurality of compounds, for creating a virtual MS$^n$ spectrum in which the standard MS$^n$ spectra corresponding to the candidate compounds included in the assumed combination are integrated with each other, and for calculating the degree of similarity between the virtual MS$^n$ spectrum and the measured MS$^n$ spectrum for each combination of the candidate compounds, wherein the plurality of compounds is identifiable using the degree of similarity calculated by the similarity calculator.

For example, the tandem mass up spectrometry data processing system according to the present invention is used for processing MS$^n$ spectrum data obtained with a triple quadrupole mass spectrometer, Q-TOF mass spectrometer, ion trap mass spectrometer, ion-trap time-of-flight mass spectrometer or similar device, and typically, for processing MS$^2$ spectrum data.

In any of the first and second modes of the tandem mass spectrometry data processing system according to the present invention, a candidate compound for an unknown compound to be identified is searched for by a database search using a compound database in which known compound information is stored. In the first mode of the tandem mass spectrometry data processing system, the mass-to-charge ratio of the precursor ion and the peak information (which at least includes mass-to-charge ratios) of an MS$^n$ spectrum are used to perform the database search. By comparison, in the second mode of the tandem mass spectrometry data processing system, the mass-to-charge ratio of the precursor ion and the mass of the neutral loss calculated from the peak information (which at least includes mass-to-charge ratios) of an MS$^n$ spectrum are used to perform the database search.

In any of these cases, the mass-to-charge ratios of the plurality of ions collectively selected as the precursor ions (i.e. the ions falling within the predetermined mass-to-charge-ratio width for the precursor-ion selection) are previously known. Therefore, for each of these ions, the database searcher sets the mass-to-charge-ratio value of the ion as one of the search conditions and performs the database search. In this search, the peak information of the MS$^n$ spectrum or the neutral-loss mass information calculated from the peak information includes information on the product ions originating from an ion which is different from the aforementioned ion specified as one of the search conditions. Therefore, it is not always ensured that one compound can be identified with a high level of reliability. Accordingly, for each different ion selected as the precursor ion, the database searcher selects a plurality of candidate compounds which meet the conditions with a certain level of reliability.

Subsequently, the similarity calculator assumes a combination of the candidate compounds which respectively correspond to the plurality of ions collectively selected as the precursor ions: If three kinds of ions having different mass-to-charge ratios are collectively selected as the precursor ions, a combination of three candidate compounds is assumed, with one candidate compound selected for each of the three kinds of ions. In this assumption, all possible combinations may be tested. Then, the sit calculator retrieves the standard MS$^n$ spectrum for each of the candidate compounds from the compound database, creates a virtual MS$^n$ spectrum by integrating the standard MS$^n$ spectra corresponding to the candidate compounds included in the assumed combination, and calculates the degree of pattern similarity between the virtual MS$^n$ spectrum and the measured MS$^n$ spectrum.

If the candidate compounds included in the assumed combination are true compounds, the degree of pattern similarity between the virtual and measured MS$^n$ spectra will be high. Accordingly, the degree of similarity is calculated in the previously described manner for every possible combination of the candidate compounds. Then, for example, the calculated result is visually presented to users so that they can refer to the degrees of similarity and identify the compounds. Needless to say, for example, it is also possible to output, as the identification result, the candidate compounds included in the combination which shows the highest degree of similarity.

In the previously described manner, with the first or second mode of the tandem mass spectrometry data processing system according to the present invention, a plurality of different compounds can be identified with a high degree of certainty b d on an MS$^n$ spectrum in which the product ions generated by the dissociation of those compounds appear in a mixed form.

Advantageous Effects of the Invention

With the first or second mode of the tandem mass spectrometry data processing system according to the present invention, a plurality of different compounds can be identified with a high degree of certainty based on an MS$^n$ spectrum in which the product ions generated by the dissociation of those compounds appear in a mixed form.

BRIEF DESCRIPTION OF DRAWINGS

FIG. 2 is a flowchart showing the contents of the characteristic data-processing operation in the mass spectrometry system of the first embodiment.

FIGS. 3A and 3B show one example of the mass spectrum and MS/MS spectrum observed in the case where a plurality of ions fall within a precursor ion selection window.

FIG. 6 is a flowchart showing the contents of the characteristic data-processing operation in the mass spectrometry system of the second embodiment.

FIGS. 7A and 7B are model diagrams for explaining the characteristic data-processing operation in the mass spectrometry system of the second embodiment.

FIGS. 9A-9C show one example of the case in which the characteristic data-processing operation in the mass spectrometry system of the third embodiment is applied.

DESCRIPTION OF EMBODIMENTS

First Embodiment

One embodiment (first embodiment) of the mass spectrometry system using a tandem mass up spectrometry data processing system according to the present invention is hereinafter described with reference to the attached drawings.

Figure 1:
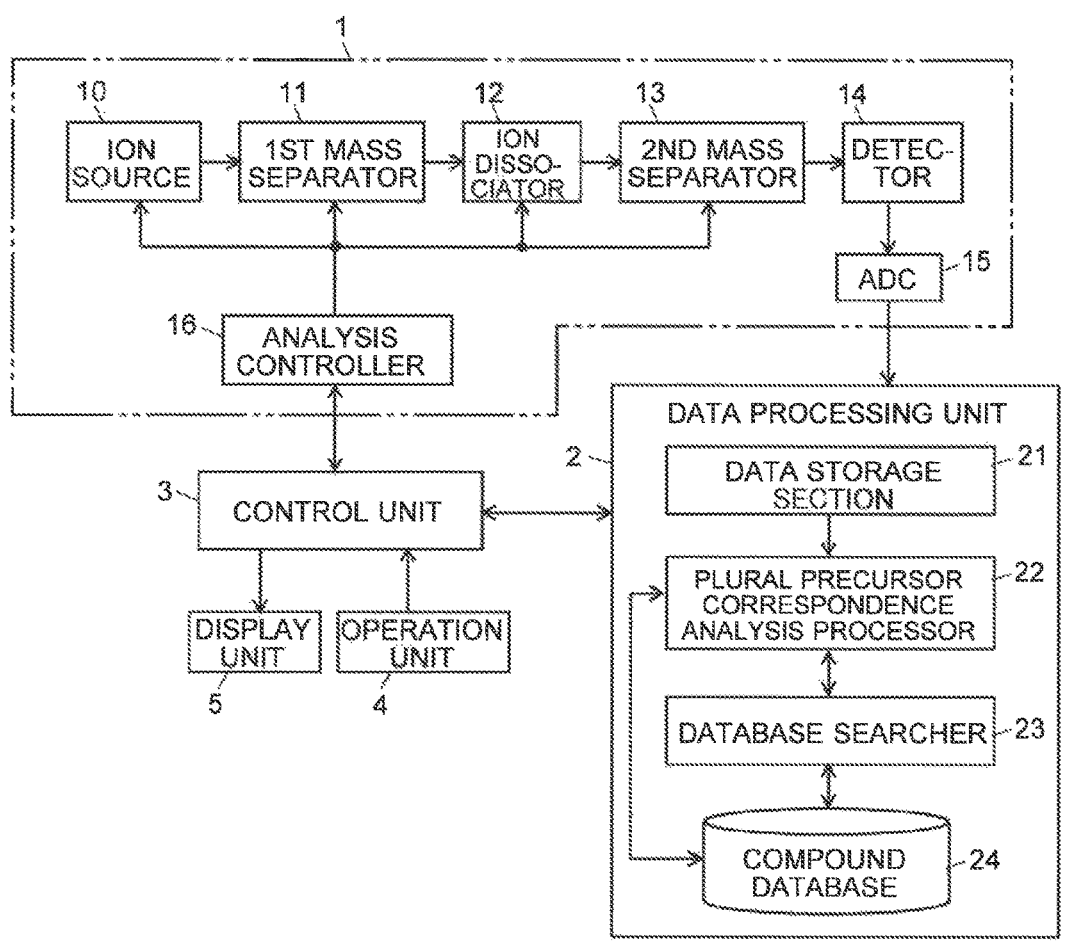
FIG. 1 is a schematic configuration diagram of a mass spectrometry system of the first embodiment using a tandem mass spectrometry data processing system according to the present invention.

FIG. 1 is a schematic configuration diagram of the mass spectrometry system of the first embodiment.

The mass spectrometry system of the first embodiment has a tandem mass spectrometer 1 including an ion source 10, a first mass separator 1, an ion dissociator 12, a second mass separator 13, a detector 14, an analogue-to-digital converter (ADC) 15 and an analysis controller 16 in order to collect the data to be processed. Under the command of the analysis controller 16, the ion source 10 ionizes the compounds contained in an introduced sample. The first mass separator 11 selects, as precursor ions, specific ions whose mass-to-charge ratios fall within a precursor-ion selection window having a predetermined mass-to-charge-ratio width among the various ions generated by the ion source 11. The ion dissociator 12 dissociates the selected precursor ions by a collision-induced dissociation or similar process. The second mass separator 13 separates the various product ions generated by the dissociation according to their mass-to-charge ratios. The detector 14 detects the separated product ions and produces a detection signal corresponding to the amount of each kind of ion. The detection signal is converted into digital data through the analogue-to-digital converter 15 and fed to a data processing unit 2.

If the tandem mass spectrometer 1 is a Q-TOF mass spectrometer, the first mass separator 11 is a quadrupole mass filter, the ion dissociator 12 is a collision cell, and the second mass separator 13 is a time-of-flight mass analyzer. If the tandem mass spectrometer 1 is an ion-trap time-of-flight mass spectrometer, the first mass separator 11 and ion dissociator 12 is an ion trap, while the second mass separator 13 is a time-of-flight mass analyzer. The ionization method used in the ion source 10 is not specifically limited; any appropriate ionization method can be used according to the form of the sample (i.e. gas sample, liquid sample, etc.).

The data processing unit 2 includes the following functional blocks: a data storage section 21 for holding a collection of data sequentially fed from the tandem mass spectrometer 1; a plural precursor correspondence analysis processor 22 for performing a characteristic data-processing operation based on the data stored in the data storage section 21, in order to identify the compounds contained in a sample; a compound database 24 in which information related to known compounds are previously registered; and a database searcher 23 for extracting candidates of a compound by a database search using the compound database 24. The control unit 3, to which an operation unit 4 and display unit 5 serving as the user interface are connected, is responsible for controlling the entire system for an actual analysis in the tandem mass spectrometer 1 as well as the data processing in the data processing unit 2.

At least a portion the control unit 3, analysis controller 16 and data processing unit 2 can be configured using a personal computer or a more powerful workstation as a hardware resource, with their respective functions realized by executing, on the computer, a dedicated controlling and processing software program previously installed on the same computer.

FIG. 3A shows one example of the mass spectrum obtained in the case where neither the precursor ion selection in the first mass separator 11 nor the ion-dissociating operation in the ion dissociator 12 is performed. When a time-of-flight mass analyzer or similar device with a high level of precision and resolving power is used as the second mass separator 13, even the ion peaks which originate from a plurality of compounds located extremely close to each other with a mass-to-charge-ratio difference of 0.5 Da or smaller will be separately observed. In the example of FIG. 3A, there are two peaks located extremely close to each other, i.e. peak A (m/z 385), which originates from compound A, and peak B (m/z 385.2), which originates from compound B. In this manner, even the plurality of peaks located close to each other are sufficiently resolved on the mass spectrum, and the mass-to-charge-ratio values corresponding to the individual peaks can be accurately determined.

On the other hand, in order to secure a sufficient amount of target ions for the dissociating operation in the MS/MS analysis, the precursor ion selection window used for selecting the precursor ions needs to have a minimum mass-to-charge-ratio width of approximately 0.5 Da. Therefore, the peaks A and B, which are extremely close to each other, cannot be separated in the precursor ion selection process. As a result, when the MS/MS analysis is performed with the precursor ion selection window set so as to include both peaks A and B, the molecular ions originating from compound A and those originating from compound B are simultaneously dissociated. Consequently, as shown in FIG. 3B, the product ions resulting from the dissociation of the two different ion species appear in a mixed form in the MS/MS spectrum.

Figure 4:
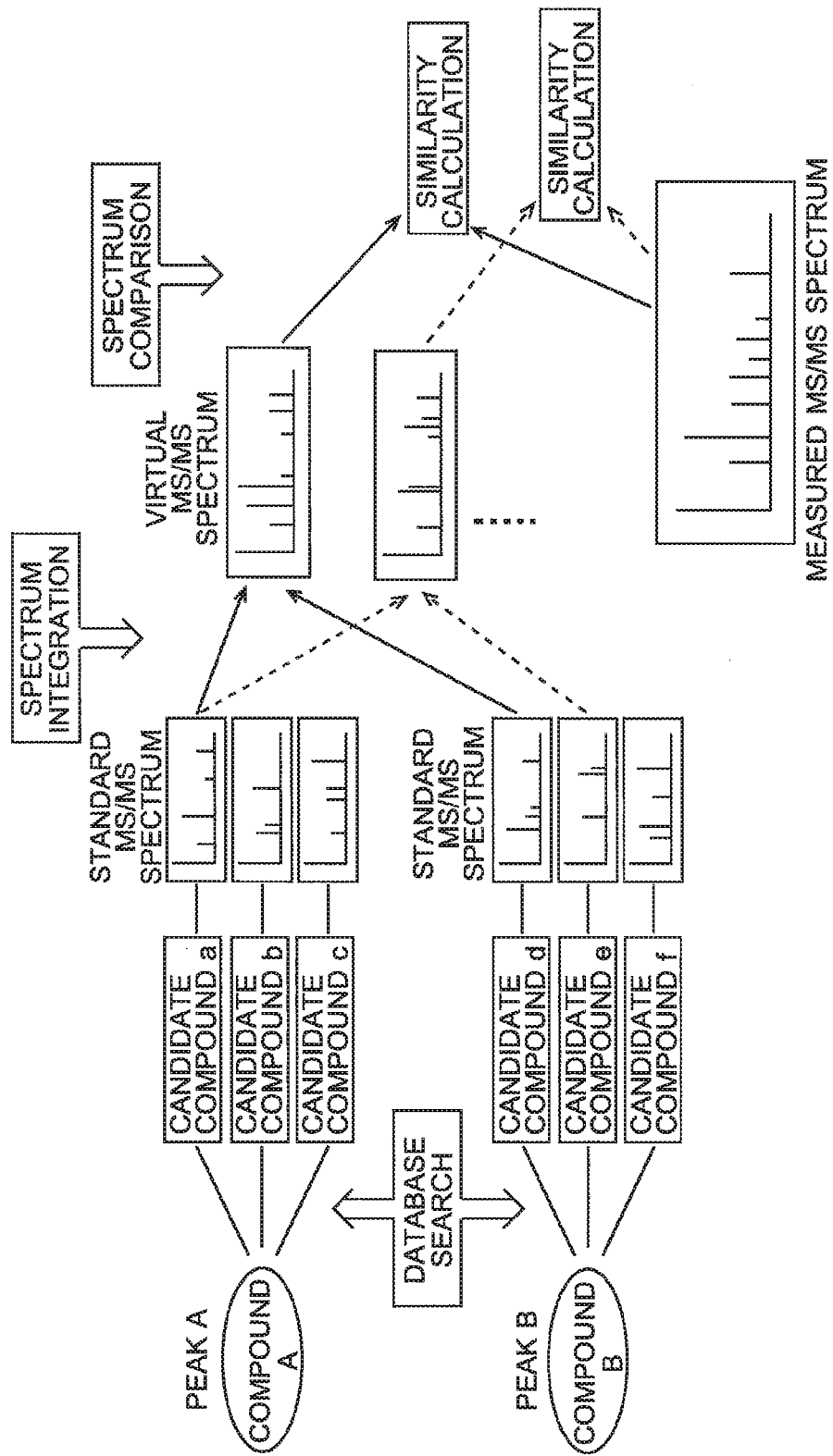
FIG. 4 is a model diagram for explaining the characteristic data-processing operation in the mass spectrometry system of the first embodiment.

The data processing unit 2 in the mass spectrometry system of the present embodiment can identify each of the compounds A and B with a high level of certainty by performing a characteristic data-processing operation (which will be hereinafter later) on the MS/MS spectrum data. FIG. 2 is a flowchart showing the steps of this characteristic data-processing operation, and FIG. 4 is a model diagram for explaining the same data-processing operation. The following description deals with the case of processing the data constituting the mass spectrum shown in FIG. 3A and those constituting the MS/MS spectrum shown in FIG. 3B, with both sets of data stored in the data storage section 21.

When the command to initiate the data processing is given, the plural precursor correspondence analysis controller 22 in the data processing unit 2 reads the measured MS/MS spectrum data to be processed from the data storage section 21, and performs a peak detection process on the MS/MS spectrum to collect information on the peaks (mass-to-charge-ratio values and signal intensity values) located in the MS/MS spectrum (Step S1). As already stated, the peak information of the product ions collected in this step does not correspond to a single precursor ion; it corresponds to the plurality of precursor ions whose mass-to-charge ratios fall within the precursor ion selection window (in the present example, m/z 385 and 385.2).

The plural precursor correspondence analysis processor 22 also reads the measured mass spectrum data from the data storage section 21, and determines the mass-to-charge-ratio value of peak A originating from compound A as well as that of peak B originating from compound B selected as the precursor ions in the MS/MS analysis. Then, the database searcher 23 sets the search conditions including the mass-to-charge-ratio value of peak A (in the present example, m/z 385) as the precursor-ion information for the database search and the peak information collected from the MS/MS spectrum in Step S1 as the product-ion information, and performs the database search over the compound database 24 according to the search conditions (Step S2).

The database search is performed in a similar manner to a conventional database search for compound identification: An index value showing the similarity of the peak pattern is calculated based on the degree of matching of the mass-to-charge-ratio values of the peaks (or other kinds of information), and a plurality of compounds which yield high index values are extracted as candidate compounds. Additionally, standard MS/MS spectra corresponding to the extracted candidate compounds are read from the compound database 24 (Step S3). In the present example, it is assumed that three candidate composites "a", "b" and "c" as shown in FIG. 4 have been extracted by the database search using the mass-to-charge-ratio value of peak A originating from compound A as the precursor-ion information.

Next, the database searcher 23 sets the search conditions with the mass-to-charge-ratio value of peak B (in the present example, m/z 385.2) as the precursor-ion information for the database search and the peak information collected from the MS/MS spectrum in Step S1 as the product-ion information, and performs the database search over the compound database 24 according to these search conditions (Step S4). As a result of this database search, a plurality of compounds are extracted as candidate compounds, and standard MS/MS spectra corresponding to the extracted candidate compounds are read from the compound database 24 (Step S5). In the present example, it is assumed that three candidate composites "d", "e" and "f" as shown in FIG. 4 have been extracted by the database search using the mass-to-charge-ratio value of peak B originating from compound B as the precursor-ion information.

Subsequently, the plural precursor correspondence analysis processor 22 selects one of the candidate compounds extracted for peak A as well as one of those extracted for peak B, and creates a virtual MS/MS spectrum by integrating the two standard MS/MS spectra which respectively correspond to the two candidate compounds included in the present combination of the candidate compounds. The virtual MS/MS spectrum can be created by simply adding the peaks on the standard MS/MS spectra. Then, the plural precursor correspondence analysis processor 22 calculates the degree of similarity in the peak pattern between the virtual MS/MS spectrum and the measured MS/MS spectrum. In this manner, the degree of similarity in the peak pattern between the virtual and measured MS/MS spectra is determined for one combination of the candidate compounds (Step S6).

Then, whether or not the calculation of the degree of similarity has been completed for all possible combinations of the candidate compounds is determined (Step S7). If there remains a combination of the candidate compounds for which the degree of similarity has not been calculated yet, the operation returns to Step S6. By repeating Steps S6 and S7, the degree of similarity between the virtual and measured MS/MS spectra is determined for every possible combination: in the present example, for every possible combination of the three compound candidates "a", "b" and "c" extracted for compound A with the three compound candidates "d", "e" and "f" extracted for compound B shown in FIG. 4, or specifically, for each of the nine combinations of (a, d), (a, e), (a, f), (b, d), (b, e), (b, f), (c, d), (c e) and (c, f).

If the candidate compounds selected as the combination are actually the compounds A and B, the deuce of similarity between the virtual and measured MS/MS spectra should be high. In other words, based on this degree of similarity, whether or not the selected candidate compounds are the correct compounds can be determined. Accordingly, the plural precursor correspondence analysis processor 22 displays the process results, i.e. the names of the candidate compounds and the degree of similarity, in descending order of the degree of similarity calculated in Step S6 on the screen of the display unit 5 via the control unit 3 (Step S8). Ultimately, the user views the displayed results and identifies the plurality of compounds A and B selected as the precursor ions.

The previous description is concerned with the case where two ions are included within the precursor ion selection window. It is evident that the previously described process can also be similarly applied to identify a plurality of compounds in the case where there three or more ion species are included within the precursor ion selection window and those ion species are collectively dissociated as precursor ions.

In the mass spectrometry system of the first embodiment, the peak information derived from the measured MS/MS spectrum i.e. the mass-to-charge-ratio values (or the mass-to-charge-ratio values and signal intensity values) of the product ions are used in the process of searching for the candidate compounds by the database search. It is also possible to perform a similar database search using the mass of a neutral loss.

The mass of a neutral loss is the difference between the mass-to-charge ratio of a precursor ion and that of a product ion. Therefore, when the mass-to-charge-ratio value of peak A originating from compound A is set as the precursor-ion information for the database search, the difference between the mass-to-charge ratio of peak A and that of a product ion can be used as a neutral-loss mass in the database search. Similarly, when the mass-to-charge-ratio value of peak B originating from compound B is set as the precursor-ion information for the database search, the difference between the mass-to-charge ratio of peak B and that of a product ion cart be used as a neutral-loss mass in the database search. After the candidate compounds for each peak are extracted by the database search, the previously described process of creating a virtual MS/MS spectrum, calculating the degree of similarity between the virtual and measured MS/MS spectra, and displaying the results in descending order of the degree of similarity can be similarly performed as described in the first embodiment.

In the first embodiment, the candidate compounds and other results are displayed in descending order of the degree of similarity. Alternatively, the result which gives the highest degree of similarity may be regarded as the correct result and be solely displayed. It is also possible to determine whether or not the degree of similarity exceeds a predetermined threshold, and eventually display a message of "no matches (not identifiable)" if there is no combination of the candidate compounds which exceeds the threshold.

Second Embodiment

An embodiment (second embodiment) of the mass spectrometry system using a tandem mass spectrometry data processing system which is not included in, but is related to the present invention is hereinafter described with reference to the attached drawings.

Figure 5:
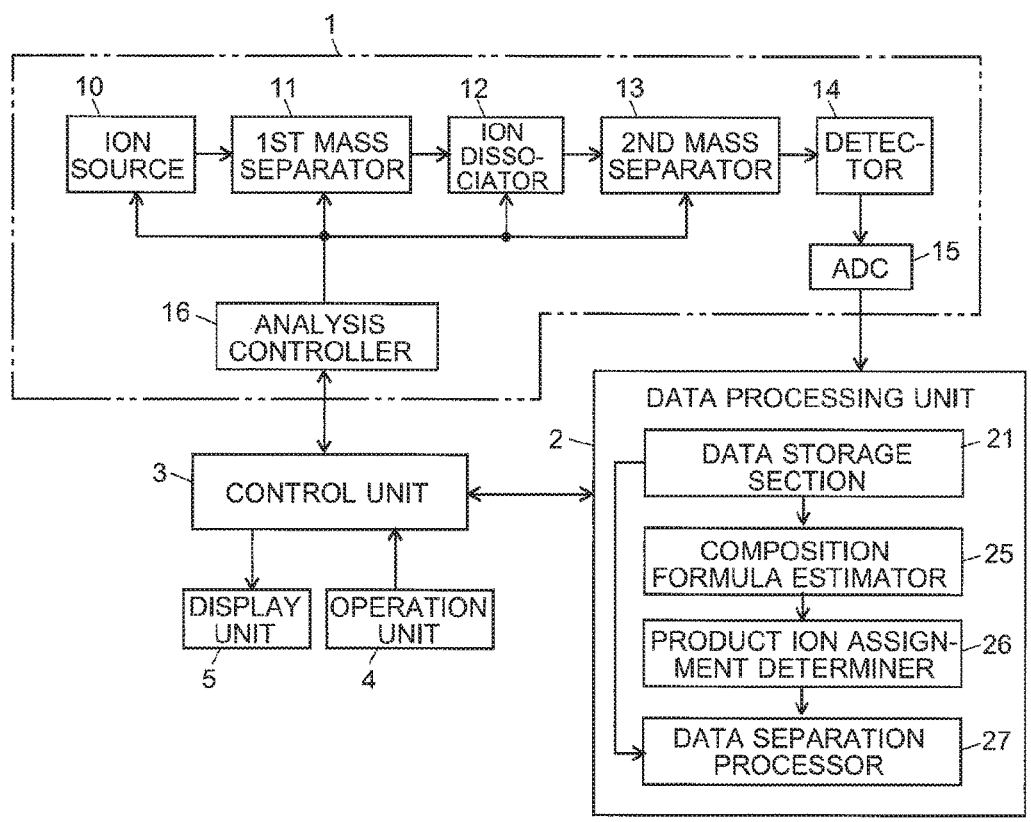
FIG. 5 is a schematic configuration diagram of a mass spectrometry system of the second embodiment using a tandem mass spectrometry data processing system related to the present invention.

FIG. 5 is a configuration diagram of the mass spectrometry system of the second embodiment. The same components as used in the mass spectrometry system of the first embodiment are denoted by the same numerals. More specifically, the mass spectrometry system of the second embodiment differs from the first embodiment in that the data processing unit 2 has different functional blocks, while the configurations of the tandem mass analyzer 1 and other sections are identical to the first embodiment.

In the mass spectrometry system of the second embodiment, the data processing unit 2 includes a composition formula estimator 25, a product ion assignment determiner 26 and a data separation processor 27 as its functional blocks, in addition to the data storage section 21.

FIG. 6 is a flowchart showing the contents of the characteristic data-processing operation in the mass spectrometry system of the second embodiment. FIGS. 7A and 7B are model diagrams for explaining this characteristic data-processing operation. The process performed in the data processing unit 2 is hereinafter described.

When the data-processing operation is initiated, the composition formula estimator 25 reads measured mass spectrum data from the data storage section 21, and determines the mass-to-charge-ratio value of peak A originating from compound A as well as that of peak B originating from compound B selected as the precursor ions. For each of the compounds A and B, the composition formula estimator 5 estimates the composition formula, i.e. the kinds of elements constituting the compound as well the number of atoms of each element, from the determined mass-to-charge-ratio values (Step S11). As already noted, if the second mass separator 13 is a time-of-flight mass analyzer or similar device with a high level of precision and resolving power, the mass-to-charge-ratio values can be determined with a high level of accuracy, so that the composition formula can be estimated with a high level of certainty.

Next, the composition formula determiner 25 also reads measured MS/MS spectrum data from the data, storage section 21 and performs peak detection process on the MS/MS spectrum to collect the mass-to-charge-ratio values of the peaks located on the MS/MS spectrum. Then, the composition formula determiner 25 estimates the composition formula of each product ion observed on the MS/MS spectrum from the determined mass-to-charge-ratios (Step S12).

Normally, if the target is an organic compound, its composition formula is estimated on the assumption that H, C, O, N and other fundamental elements are contained in it. In the case where a special element, such as a halogen (e.g. Cl or Br), is contained, the estimation of the composition formula will be easy if additional information which indicates the potential presence of such an element is provided. Accordingly, it is preferable to allow users to input such additional information and utilize the information for the estimation of the composition formula.

In normal situations, a product ion is a certain fragment (chemical structure) desorbed from the original precursor ion. Therefore, the composition formula of a product ion should be a subset of the composition formula of the original precursor ion. That is to say, the number of atoms of any element constituting the product ion should be equal to or smaller than that of the same element constituting the original precursor ion, and any element constituting the product ion should be contained in the original precursor ion. In other words, if the number of atoms of one element constituting the product ion exceeds that of the same element constituting the precursor ion, or if one of the elements constituting the product ions is not contained in the precursor ion, it is extremely likely that the precursor ion in question is not the origin of that product ion. Accordingly, for each product ion detected in the measured MS/MS spectrum, the product ion assignment determiner 26 verifies the consistency of its composition formula by determining whether or not the composition formula is a subset of any of the composition formulae of the plurality of precursor ions, and assigns the peak of the product ion to a precursor ion whose composition formula is consistent with it (Step S13). The processes of Step S13 and S14 are repeated until the assignment is determined for all product ion peaks detected in the measured MS/MS spectrum (until "Yes" in Step S14).

Needless to say, there is a good possibility that the composition formula of one product ion is a common subset of the composition formulae of a plurality of precursor ions. In that case, the product ion can be assigned to both of the precursor ions. Conversely, if there is a product ion whose composition formula is not a subset of any of the composition formulae of the precursor ions, it may actually be a noise peak and not a peak which has originated from a product ion. Such a peak can be simply excluded. After the assignment of all peaks which have originated from the product ions (to be exact, all peaks which are considered to be the product ions) detected from the MS/MS spectrum in Step S12 is determined, the data separation processor 27 separates the MS/MS spectrum data into groups corresponding to the precursor ions based on the assignment result (Step S15). Furthermore, based on the separated data, the data separation processor 27 creates MS/MS spectra each of which corresponds to one of the precursor ions (Step S16).

FIG. 7A shows one example in which the peaks located in an MS/MS spectrum have been assigned, in which the square (□) and circle (○) represent the precursor ion to which each peak has been assigned. The peaks with no symbol are those which have not been assigned to any precursor ion. FIG. 7B shows an example of the MS/MS spectrum separated into two spectra based on the assignment result. As for the product ion assigned to both of the precursor ions, there are two possibilities: the product ion has truly originated from both precursor ions, or one of the assignments to the precursor ions is incorrect (or rarely, both assignments are incorrect). In the latter case, a false peak will appear on the separated MS/MS spectra. However, since any peak which is evidently different from the product ions is removed, it is possible to obtain an MS/MS spectrum which is purer and more useful than the unseparated MS/MS spectrum at the very least.

For example, after the MS/MS spectra separated for each precursor ion are obtained in this manner, the peak information extracted from each of those MS/MS spectra can be used for the database search to identify the compounds. Since the peak information used in this database search is free of at least a portion of the product-ion peaks which have originated from unrelated precursor ions, the database search provides the result with improved accuracy and makes it more likely that the correct compound is identified.

Third Embodiment

Another embodiment (third embodiment) of the mass spectrometry system using a tandem mass spectrometry data processing system which is not included in, but is related to the present invention is hereinafter described with reference to the attached drawings.

Figure 8:
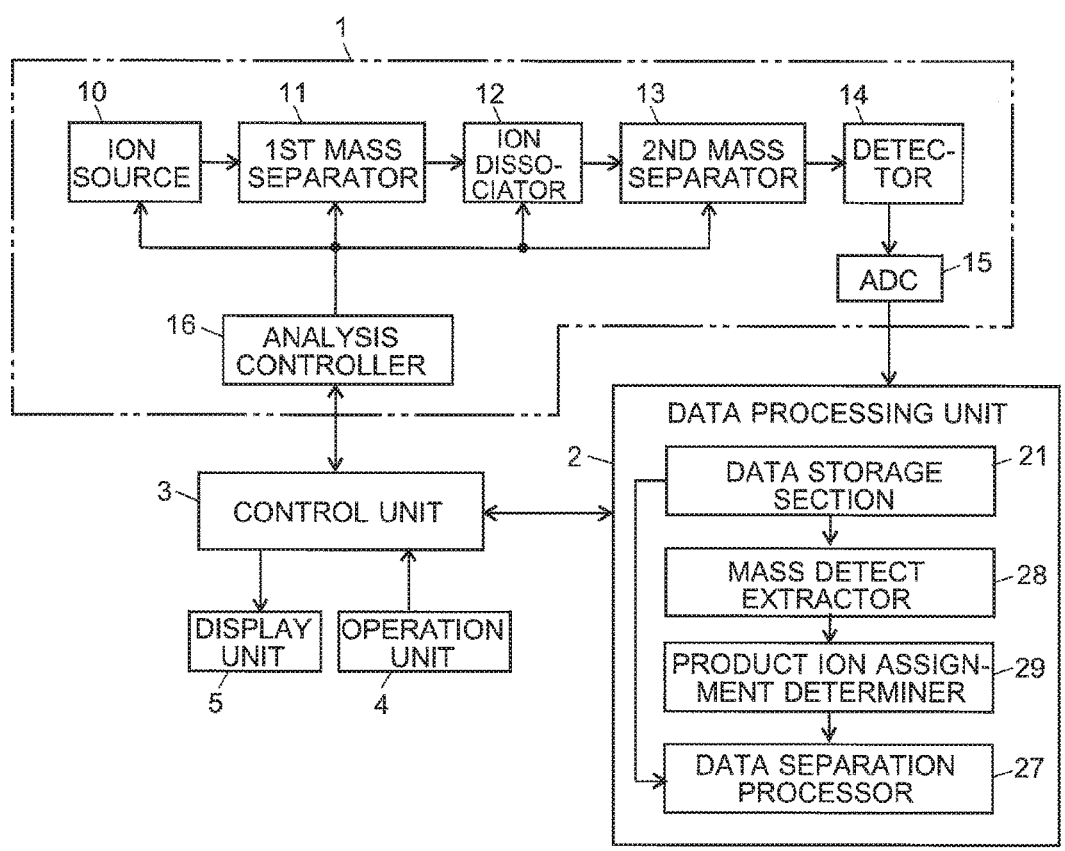
FIG. 8 is a schematic configuration diagram of a mass spectrometry system of the third embodiment using a tandem mass spectrometry data processing system according related to the present invention.

FIG. 8 is a configuration diagram of the mass spectrometry system of the third embodiment. The same components as used in the mass spectrometry system of the first or second embodiment are denoted by the same numerals. More specifically, the mass spectrometry system of the third embodiment differs from the first or second embodiment in that the data processing unit 2 has different functional blocks, while the configurations of the tandem mass analyzer 1 and other sections are identical to the first or second embodiment.

In the mass spectrometry system of the third embodiment, the data processing unit 2 includes a mass defect extractor 28 and a product ion assignment determiner 29 as its functional blocks, in addition to the data storage section 21 and the data separation processor 27.

The third embodiment is similar to the second embodiment in that each of the product ion peaks detected in the measured MS/MS spectrum is assigned to one (or more) of the precursor ions. The difference exists in that a technique which is generally called the "mass defect filtering" is used in the assignment process. This technique is frequently applied in a metabolite analysis using mass spectrometry. It utilizes the closeness of the value after the decimal point of the try mass-to-charge-ratio value (i.e. the mass defect) to distinguish between unnecessary ions and useful ions.

The fact that the mass defect filtering is useful for finding the precursor ion from which a product ion has been derived is hereinafter described with reference to FIGS. 9A-9C.

Consider the case where the sample contains two compounds as shown in FIG. 9A, i.e. Triallate (S-2,3,3-trichloroallyl di-isopropyl thiocarbamate) and Fenpropimorph ((2β,6β)-4-[3-[4-(1,1-dimethylethyl) Phenyl]-2-methylpropyl]-2,6-dimethylmorpholine). The mass of Triallate is 304.0091, and that of Fenpropimorph is 304.2635. The molecular ions originating from these two compounds have an extremely small mass-to-charge-ratio difference of 0.2544 Da on the mass spectrum. Therefore, as already explained, it is impossible to isolate each of the ions originating from these two compounds through the precursor ion selection window which is set for the MS/MS analysis, so that the ions originating from the two compounds will be collectively dissociated as the precursor ions. Consequently, the product ions originating from both compounds appear in a mixed form on the MS/MS spectrum.

When Triallate is dissociated, an ion having a chemical structure as shown in FIG. 9B is generated as one of the productions. On the other hand, when Fenpropimorph is dissociated, an ion having a chemical structure as shown in FIG. 9C is generated as one of the product ions. The mass defect of the former product ion is 0.0405 Da, and that of the latter product ion is 0.3245 Da. On the other hand, the mass defect of Triallate is 0.0091 Da, and that of Fenpropimorph is 0.2635 Da. Comparing these values demonstrates that the mass defect of each product ion is close to that of the parent compound observed before the dissociation. Needless to say, such a judgment is premised on that the mass defects of the plurality of compounds collectively selected as the precursor ions differ from each other to a certain extent. Provided this condition is met, it is possible to assign each product ion to one precursor ion, i.e. to one compound, by determining which compound among the plurality of the compounds has a mass defect that is close to the mass defect of the product ion concerned.

Accordingly, in the mass spectrometry system of the third embodiment, the mass defect extractor 28 determines the mass defects of the precursor ions and product ions. The product ion assignment determiner 29 determines the assignment of each product ion by finding a precursor ion whose mass defect is close to that of the product ion. However, depending on the form of dissociation, the product ion may have a mass defect that is not close to the original precursor ion. Therefore, for example, it is preferable to adopt the rule that, if the smallest value of the mass-defect difference between a product ion and the precursor ions has exceeded a predetermined threshold, that product ion should be assigned to none of the precursor ions or conversely, to both of the precursor ions. After the assignment of the product ions are determined in this manner, the MS/MS spectrum data can be separated based on the assignment result, similarly to the second embodiment.

The second and third embodiments can be used in combination; i.e. when determining the assignment of the product ions, it is possible to use both the estimated composition formula and the mass defect to improve the accuracy of the assignment.

It should be noted that the first embodiments is a mere example of the present invention, and any change, modification or addition appropriately made within the spirit of the present invention will evidently fall within the scope of claims of the present application.

REFERENCE SIGNS LIST

1 . . . Tandem Mass Spectrometer
10 . . . Ion Source
11 . . . First Mass Separator
12 . . . Ion Dissociator
13 . . . Second Mass Separator
14 . . . Detector
15 . . . Analogue-to-Digital Converter
16 . . . Analysis Controller
2 . . . Data Processing U
21 . . . Data Storage Section
22 . . . Plural Precursor Correspondence Analysis Processor
23 . . . Database Searcher
24 . . . Compound Database
25 . . . Composition Formula Estimator
26, 29 . . . Product Ion Assignment Determiner
27 . . . Data Separation Processor
28 . . . Mass Defect Extractor
3 . . . Control Unit
4 . . . Operation Unit
5 . . . Display Unit

The invention claimed is:

1. A tandem mass spectrometry data processing system for processing $MS^n$ spectrum data obtained by performing a mass spectrometry for product ions obtained by dissociating ions collectively selected as precursor ions, the precursor ions originating from a plurality of different compounds and having mass-to-charge ratios within a predetermined mass-to-charge-ratio width, the system comprising:
 a) a compound database in which at least information on standard $MS^n$ spectra related to known compounds is stored;
 b) a peak information collector for collecting peak information from an $MS^n$ spectrum created based on the $MS^n$ spectrum data obtained by an actual measurement;
 c) a database searcher for finding a candidate compound for each of the ions of the plurality of compounds selected as the precursor ions, by performing a database search over the compound database based on a mass-to-charge-ratio value of the ion concerned and the peak information collected from an $MS^n$ spectrum by the peak information collector; and
 d) a similarity calculator for retrieving, from the compound database, the standard $MS^n$ spectra for the candidate compounds selected for each of the ions of the plurality of compounds, for assuming a combination of the candidate compounds for the plurality of compounds, for creating a virtual $MS^n$ spectrum in which the standard $MS^n$ spectra corresponding to the candidate compounds included in the assumed combination are integrated with each other, and for calculating a degree of similarity between the virtual $MS^n$ spectrum and the measured $MS^n$ spectrum for each combination of the candidate compounds,
 wherein the plurality of compounds is identifiable using the degree of similarity obtained by the similarity calculator.

2. A tandem mass spectrometry data processing system for processing $MS^n$ spectrum data obtained by performing a mass spectrometry for product ions obtained by dissociating ions collectively selected as precursor ions, the precursor ions originating from a plurality of different compounds and having mass-to-charge ratios within a predetermined mass-to-charge-ratio width, the system comprising:
 a) a compound database in which at least information on standard $MS^n$ spectra related to known compounds is stored;
 b) a peak information collector for collecting peak information from an $MS^n$ spectrum created based on the $MS^n$ spectrum data obtained by an actual measurement;
 c) a database searcher for finding a candidate compound for each of the ions of the plurality of compounds selected as the precursor ions, by calculating a mass of a neutral loss which is a difference between a mass-to-charge-ratio value of the ion concerned and a mass-to-charge ratio known from the peak information collected from an $MS^n$ spectrum by the peak information collector, and performing a database search over the compound database based on the mass-to-charge ratio of the precursor ion concerned and the mass of the neutral loss; and
 d) a similarity calculator for retrieving, from the compound database, the standard $MS^n$ spectra for the candidate compounds selected for each of the ions of the plurality of compounds, for assuming a combination of the candidate compounds for the plurality of compounds, for creating a virtual $MS^n$ spectrum in which the standard $MS^n$ spectra corresponding to the candidate compounds included in the assumed combination are integrated with each other, and for calculating a degree of similarity between the virtual $MS^n$ spectrum and the measured $MS^n$ spectrum for each combination of the candidate compounds,
 wherein the plurality of compounds is identifiable using the degree of similarity calculated by the similarity calculator.

* * * * *